(12) United States Patent
Baxter et al.

(10) Patent No.: US 6,313,309 B1
(45) Date of Patent: Nov. 6, 2001

(54) 4-THIONAPHTHYL—1H—IMIDAZOLES WHICH ARE USEFUL $\alpha_2$2-ADRENOCEPTOR AGONISTS/ ANTAGONISTS

(75) Inventors: Ellen W. Baxter, Glenside; Robert E. Boyd, Horsham; Michelle C. Jetter, Norristown, all of PA (US); Mark McDonnell, Raritan, NJ (US); Allen B. Reitz, Lansdale; Tina Morgan Ross, Audubon, both of PA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 09/286,395

(22) Filed: Apr. 5, 1999

(51) Int. Cl.[7] ................... C07O 233/54; A61K 31/4178; A61N 29/00
(52) U.S. Cl. ......................................... 548/311.4; 514/397
(58) Field of Search ........................... 548/311.4; 514/397

(56) References Cited

U.S. PATENT DOCUMENTS 4,663,344 * 5/1987 Durette et al. ........................ 514/443
5,905,088 * 5/1999 Diaz et al. ........................... 514/468

FOREIGN PATENT DOCUMENTS

0129478 * 12/1984 (EP) .

* cited by examiner

Primary Examiner—Floyd D. Higel
(74) Attorney, Agent, or Firm—John Harbour

(57) ABSTRACT

4-thionaphthyl-1H-imidazoles are $\alpha_2$-adrenoceptor agonists/antagonists. As delta-opioid receptor agonists, such compounds are useful as analgesics. Depending on their agonist/antagonist effect, such compounds may also be useful agents to treat hypertension, glaucoma, sexual dysfunction, depression, attention deficit hyperactivity disorder, the need for anesthesia or cardiac arrythmia.

8 Claims, No Drawings

4-THIONAPHTHYL—1H—IMIDAZOLES WHICH ARE USEFUL α₂-ADRENOCEPTOR AGONISTS/ANTAGONISTS

The present invention relates to $\alpha_2$-adrenoceptor agonists/antagonists. More particularly, the present invention relates to certain 4-thionaphthyl-1H-imidazoles and analogues which are $\alpha_2$-adrenoceptor agonists having analgesic activity.

BACKGROUND OF THE INVENTION $\alpha_2$-adrenoceptor agonists/antagonists are useful to treat a variety of conditions, including, hypertension, glaucoma, sexual dysfunction, depression, attention deficit hyperactivity disorder, the need for anesthesia, cardiac arrythmia and the need for analgesia. Particularly, $\alpha_2$-adrenoceptor agonists are well known analgesics.

Clonidine is a centrally acting $\alpha_2$-adrenoceptor agonist with wide clinical utility as an antihypertensive agent. Clonidine is believed to act by inhibiting the release of norepinephrine from sympathetic nerve terminals via a negative feedback mechanism involving $\alpha_2$-adrenoceptors located on the presynaptic nerve terminal. This action is believed to occur in both the central (CNS) and peripheral (PNS) nervous systems. More recently, the role of $\alpha_2$-adrenoceptor agonists as analgesic agents in humans and antinociceptive agents in animals has been demonstrated. Clonidine and other $\alpha_2$-adrenoceptor agonists have been shown to produce analgesia through a non-opiate mechanism and, thus, without opiate liability. However, other behavioral and physiological effects were also produced, including sedation and cardiovascular effects.

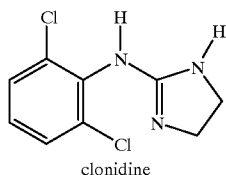

clonidine

Medetomidine, detomidine, and dexmedetomidine are $\alpha_2$-adrenoceptor agonists. Dexmedetomidine is used clinically in veterinary medicine as a sedatives/hypnotic for pre-anaesthesia. These compounds are hypotensive in animals and in humans, but the magnitude of this cardiovascular effect is relatively insignificant.

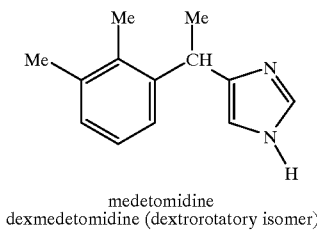

medetomidine
dexmedetomidine (dextrorotatory isomer)

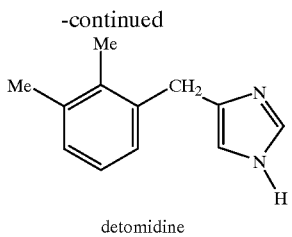

detomidine

U.S. Pat. No. 3,574,844, Gardocki et al., teach 4-[4(or 5)-imidazolylmethyl]-oxazoles as effective analgesics. The disclosed compounds are of the general formula:

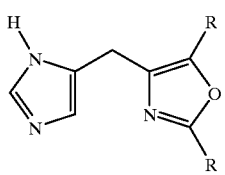

compounds of this type are insufficiently active and suffer from unwanted side effects.

U.S. Pat. No. 4,913,207, Nagel et al., teach arylthiazolylimidazoles as effective analgesics. The disclosed compounds are of the general formula:

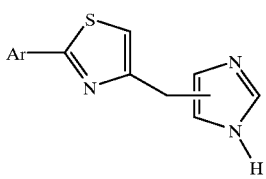

Compounds of this type are insufficiently active and suffer from unwanted side effects.

WO92/14453, Campbell et al., teach 4-[(aryl or heteroaryl)methyl]-imidazoles as effective analgesics. The disclosed compounds are of the general formula:

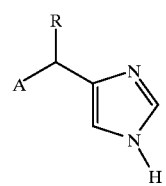

R is H or alkyl
A is aryl or heteroaryl

The disclosed compounds are insufficiently active and suffer from unwanted side effects.

Kokai No. 1-242571, Kihara et al., disclose a method to produce imidazole derivatives for use, among other uses, as antihypertensive agents.

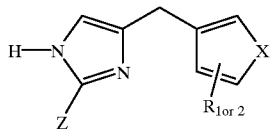

Z is H or phenyl
R is H, alkyl or halogen
X is S or O

A single mixture of compounds meeting the above formula was reportedly produced by the inventive method. This was a mixture of 4-(2-thienyl)-methylimidazole and 4-(3-thienyl)-methylimidazole represented by the following formula:

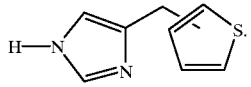

The disclosed compounds are insufficiently active and suffer from unwanted side effects.

JP-42001546 (1964) discloses a compound of the general formula:

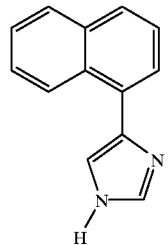

as a useful pesticide.

EP 129478 (1984) discloses a compound of the formula:

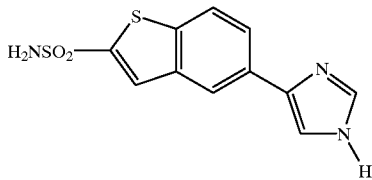

as useful in the treatment of glaucoma.

SUMMARY OF THE INVENTION

Briefly, there is provided by the present invention compounds having improved analgesic activity of the formula:

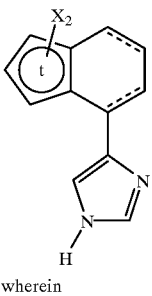

wherein

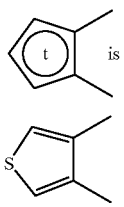 is selected from the group consisting of , 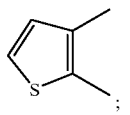 and 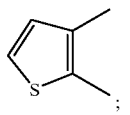 and X is independently selected from the group consisting of hydrogen, $C_{1-4}$alkyly, bromine, chlorine, iodide, trifluoromethyl, $C_{1-4}$alkoxy, —$SO_2NH_2$ and nitro; with the stipulation that the six membered ring, except for the bond shared with thienyl, is fully saturated, has a single unsaturated bond in conjugation with the imidazole ring or has two unsaturated bonds.

DETAILED DESCRIPTION OF THE INVENTION

The compounds of the present invention are prepared by the methods shown in Schemes 1 and 2. In Scheme 1, thienyl ketones 2 are condensed with a Grignard reagent derived from a protected 4-iodoimidazole to give 3, or converted to the corresponding vinyl triflate reagent 7. Subsequently, Grignard addition product 3 is dehydrated to provide a site of unsaturation (viz. 4), which is followed by removal of the imidazole protecting group to give desired products 5, and then further reduced to afford products 6. Alternatively, Grignard addition product 3 is hydrogenolyzed directly to reduce the benzylic hydroxyl and remove the protecting group (e.g. the trityl or $Ph_3C$ group) to give products 6. Vinyl triflate 7 could be condensed in a Stille coupling reaction with a 4-(stannyl)imidazole in the presence of Pd(0) to give 4, or condensed with the 4-imidazo Grignard reagent described above in the presence of $ZnCl_2$ to also give 4.

The thienyl ketones 2 may be produced by methods well known to the art. In a first method, thienyl ketone 2 may be produced in three steps. In a first and second step, the appropriate thiophene acrylic acid, appropriately substituted with X, is reduced and the resulting acid converted to the acid chloride. Finally, intramolecular acylation produces the thienyl ketones 2. Alternatively, thiophene, appropriately substituted with X is acylated with ethyl succinyl chloride. Saponification of the ester, followed by Wolff-Kishner reduction provides the keto acid. This acid is then converted to the acid chloride and intramolecular acylation yields the thienyl ketones 2. Certain thienyl ketones 2 are readily available commercially.

In the case where X is hydrogen, $C_{1-4}$alkyl, $C_{1-4}$alkoxy and trifluoromethyl, the appropriately substituted thienyl ketone 2 may be produced and the substituent in question will stably endure the reactions of Scheme 1 to arrive at target products 5 and 6. In the case where X is chlorine, bromine, and nitro, product 6 may be obtained from product 5 by alternate reduction conditions such as borane/methylsulfide or triethylsilane/trifluoroacetic acid.

SCHEME 1

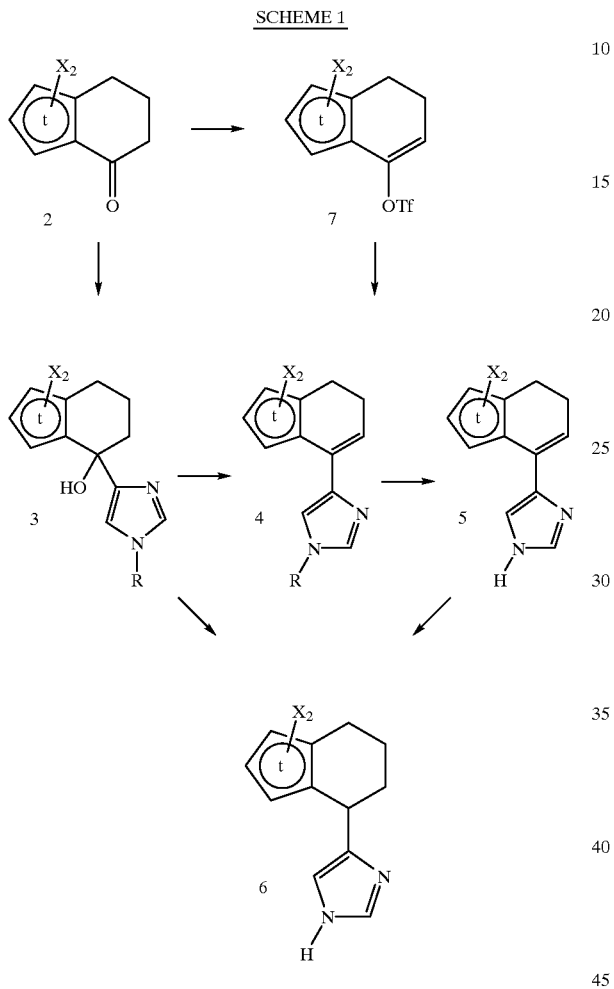

The fully aromatic analogues of products 5 and 6 may be produced by extension of Scheme 1 as shown in Scheme 1A. Vinyl imidazoles 4, can be oxidized with DDQ to yield the fully aromatic compounds 10 which can then be deprotected to give products 1.

SCHEME 1A

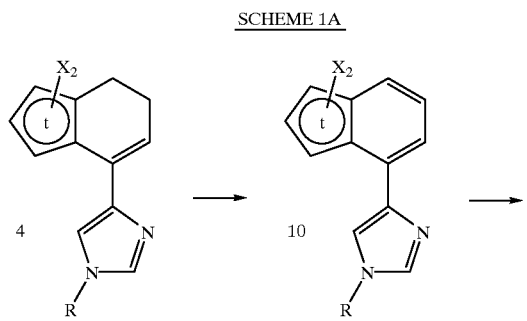

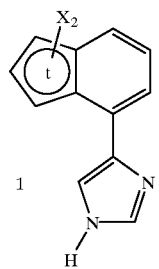

Alternatively, certain of the compounds of the invention could be prepared in a more direct manner involving the condensation of the Grignard reagent from compound 8 with ketones 9. In this manner, products 1a were obtained from 8 and 9. Ketones 9 may be produced from reaction of the Grignard reagent derived from the imidazole with an appropriately substituted thiophene aldehyde, followed by oxidation. Production of ketones 9 is generally described and specifically exemplified in U. S. Pat. No. 5,621,113 to Boyd et al.

SCHEME 2

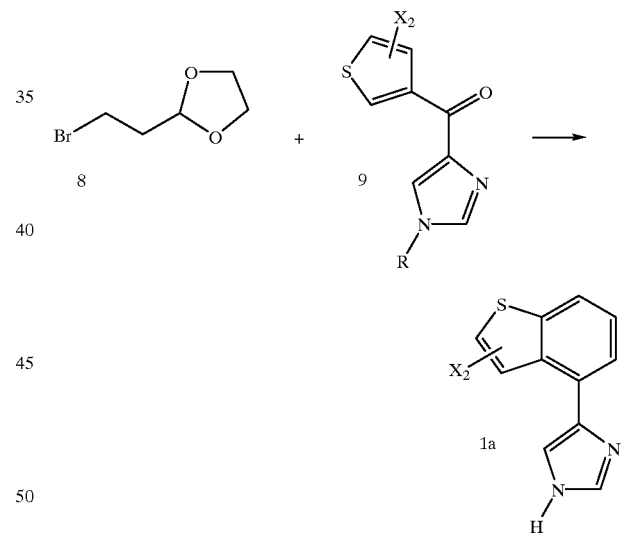

Preferred X are selected from the group consisting of hydrogen, methyl, ethyl, n-propyl, bromine, chlorine, trifluoromethyl, methoxy, ethoxy, propoxy and nitro. The most preferred X is methyl, bromine, methoxy and nitro.

The most preferred compounds of the instant invention are shown in Table I:

TABLE I

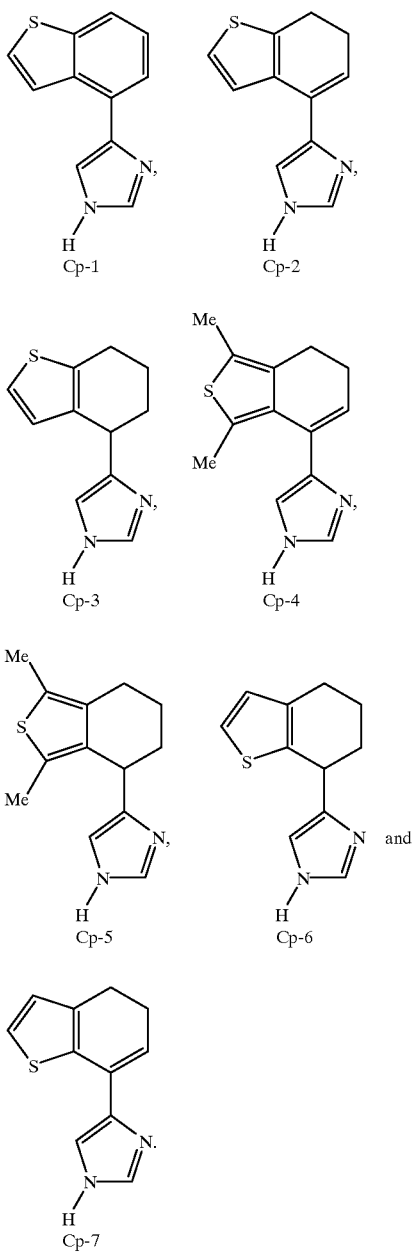

The activity of compounds of the invention as analgesics may be demonstrated by the in vivo and in vitro assays as described below:

Alpha-2D Adrenergic Receptor Binding Assay

Male, Wistar rats (150–250 g, VAF, Charles River, Kingston, N.Y.) are sacrificed by cervical dislocation and their brains removed and placed immediately in ice cold HEPES buffered sucrose. The cortex is dissected out and homogenized in 20 volumes of HEPES sucrose in a Teflon™-glass homogenizer. The homogenate is centrifuged at 1000 g for 10 min, and the resulting supernatant centrifuged at 42,000 g for 10 min. The resulting pellet is resuspended in 30 volumes of 3 mM potassium phosphate buffer, pH 7.5, preincubated at 25° C. for 30 min and recentrifuged. The resulting pellet is resuspended as described above and used for the receptor binding assay. Incubation is performed in test tubes containing phosphate buffer, 2.5 mM $MgCl_2$, aliquots of the synaptic membrane fraction, the ligand $^3$H-para-aminoclonidine and test drug at 25° C. for 20 min. The incubation is terminated by filtration of the tube contents through glass fiber filter sheets. Following washing of the sheets with 10 mM HEPES buffer, the adhering radioactivity is quantified by liquid scintillation spectrometry.

Binding of the test drug to the receptor is determined by comparing the amount of radiolabeled ligand bound in control tubes without drug to the amount of radiolabeled ligand bound in the presence of the drug. Dose-response data are analyzed with LIGAND, a nonlinear curve fitting program designed specifically for the analysis of ligand binding data. This assay is described by Simmons, R. M. A., and Jones, D. J., Binding of [$^3$H-]prazosin and [$^3$H]p-aminoclonidine to (α-Adrenoceptors in Rat Spinal Cord, Brain Research 445:338–349, 1988.

Mouse Acetylcholine Bromide-Induced Abdominal Constriction Assay

The mouse acetylcholine bromide-induced abdominal constriction assay, is described by Collier et al. in Brit. J. Pharmacol. Chem. Ther., 32: 295–310, 1968, with minor modifications was used to assess analgesic potency of the compounds herein. The test drugs or appropriate vehicle were administered orally (p.o.) and 30 minutes later the animal received an intraperitoneal (i.p.) injection of 5.5 mg/kg acetylcholine bromide (Matheson, Coleman and Bell, East Rutherford, N.J.). The mice were then placed in groups of three into glass bell jars and observed for a ten minute observation period for the occurrence of an abdominal constriction response (defined as a wave of constriction and elongation passing caudally along the abdominal wall, accompanied by a twisting of the trunk and followed by extension of the hind limbs). The percent inhibition of this response to a nociceptive stimulus (equated to % analgesia) was calculated as follows: The % Inhibition of response, i.e., % analgesia is equal to the difference between the number of control animals responding and the number of drug-treated animals responding times 100 divided by the number of control animals responding.

At least 15 animals were used for control and in each of the drug treated groups. At least three doses were used to determine each dose response curve and $ED_{50}$ (that dose which would produce 50% analgesia). The $ED_{50}$ values and their 95% fiducial limits were determined by a computer assisted probit analysis.

TABLE II

| Cpd. | Elemental Analysis Calculated (Found) | | | α-2D Binding Ki (nm) | MAIT Activity % Inhibition 30 mg/kg po |
|---|---|---|---|---|---|
| | C | H | N | | |
| Cp-1 | 56.72 (56.29) | 3.81 (3.74) | 8.72 (8.60) | 2.6 | 73 |
| | for $C_{11}H_8N_2S.C_4H_4O_4$ (maleate) | | | | |

TABLE II-continued

| Cpd. | Elemental Analysis Calculated (Found) | | | α-2D Binding Ki (nm) | MAIT Activity % Inhibition 30 mg/kg po |
|---|---|---|---|---|---|
| | C | H | N | | |
| Cp-2 | 43.38 (43.34) for $C_{11}H_{10}N_2$S.HClO$_4$.0.1H$_2$O | 3.71 (3.61) | 9.20 (9.08) | 1.5 | 100 |
| Cp-3 | 43.10 (43.20) for $C_{11}H_{12}N_2$S.HClO$_4$.0.1H$_2$O | 4.34 (4.39) | 9.14 (9.14) | 0.56 | 100 |
| Cp-4 | 58.95 (58.51) for $C_{13}H_{14}N_2$S.C$_4$H$_4$O$_4$ (maleate) | 5.24 (4.55) | 8.09 (7.72) | 0.0086 (1.2) | 40 |
| Cp-5 | 58.60 (58.55) for $C_{13}H_{16}N_2$S.C$_4$H$_4$O$_4$ (maleate) | 5.79 (5.68) | 8.04 (7.91) | 2.9 | 93 |
| Cp-6 | 63.55 (63.74) for $C_{11}H_{12}N_2$S.0.2H$_2$O | 6.01 (6.02) | 13.47 (12.78) | 0.35 | — |
| Cp-7 | 56.59 (56.46) for $C_{11}H_{10}N_2$S.C$_4$H$_4$O$_4$/0.25C$_4$H$_8$O$_2$ | 4.52 (4.74) | 8.05 (8.23) | 3 | 60 |

Based on the above results, invention compounds of the present invention may be used to treat mild to moderately severe pain in warm-blooded animals, such as, humans by administration of an analgesically effective dose. The dosage range would be from about 10 to 3000 mg, in particular about 25 to 1000 mg or about 100 to 500 mg, of active ingredient 1 to 4 times per day for an average (70 kg) human although it is apparent that activity of individual compounds of the invention will vary as will the pain being treated. In regard to the use of these $\alpha_2$-adrenoceptor agonists/antagonists to treat hypertension, glaucoma, sexual dysfunction, depression, attention deficit hyperactivity disorder, the need for anesthesia and cardiac arrythmia, a therapeutically effective dose can be determined by persons skilled in the art by use of established animal models. Pharmaceutical compositions of the invention comprise the formula (I) compounds as defined above, particularly in admixture with a pharmaceutically-acceptable carrier.

To prepare the pharmaceutical compositions of this invention, one or more compounds of the invention or salt thereof as the active ingredient, is intimately admixed with a pharmaceutical carrier according to conventional pharmaceutical compounding techniques, which carrier may take a wide variety of forms depending on the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, though other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above.

The pharmaceutically acceptable salts referred to above generally take a form in which the imidazolyl ring is protonated with an inorganic or organic acid. Representative organic or inorganic acids include hydrochloric, hydrobromic, hydroiodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benezenesulfonic, oxalic, pamoic, 2-naphthalenesulfonic, p-toluenesulfonic, cyclohexanesulfamic, salicylic or saccharic.

The following Examples illustrate the invention:

EXAMPLE 1

4-(1,3-Dimethyl-6,7-dihydrobenzo[c]thiophene-4-yl)-1H-imidazole(Z)-2-Butenedioate (Cp-4)

Ethyl magnesium bromide (15.5 mL, 15.5 mmol) was added slowly to a solution of 4-iodo-1-tritylimidazole (4.8 g, 11.1 mmol, prepared as described by Turner and Lindel, *J. Org. Chem.* 1991, 56, 5739–5740) in methylene chloride (100 mL), and stirred at room temperature. After 30 min a solution of 1,3-dimethyl-4-keto-4,5,6,7-tetrahydrobenzo[c]thiophene (2 g, 11.1 mmol, prepared as described by Cagnaiant, et. al. *Bull. Soc. Chim. France*, 1970, 322–331) in methylene chloride (10 mL) was added slowly and stirred overnight at room temperature. The reaction was diluted with EtOAc washed sequentially with NH$_4$Cl (sat'd), H$_2$O and brine. The organic layer was dried with Na$_2$SO$_4$, filtered and the solvent evaporated in vacuo to yield 4-(1-tritylimidazol-4-yl)-1,3-dimethyl-4,5,6,7-tetrahydrobenzo[c]thiophen-4-ol as brown crystals (5.1 g, 94%). mp 111–115° C. $^1$H NMR (CDCl$_3$) δ2.08 (s, 3H), 2.15 (s, 3H), 2.25 (m, 2H), 2.45 (t, 2H), 2.70 (m, 2H), 6.81 (s, 1H), 7.10 (m, 9H), 7.41 (s, 1H). MS=491 (M+H), 243 (Ph$_3$C). A sample of this material (2.55 g, 5.5 mmol), methylene chloride (50 mL), acetyl chloride (0.78 mL, 11 mmol) and triethylamine (1.53 mL, 11 mmol) was stirred overnight at room temperature under an argon atmosphere. The mixture was then treated with methylene chloride (50 mL) and washed with NaHCO$_3$ (sat'd), water, and brine. The organic layer was then dried with Na$_2$SO$_4$, filtered and the solvent was evaporated in vacuo to yield 4-(1-tritylimidazol-4-yl)-1,3-dimethyl-4,5,6,7-tetrahydrobenzothiophen-4-yl) acetate. The acetate was stirred with diazobicycloundecane (0.82 mL, 5.5 mmol) in a mixture of benzene/MeOH (4:1, 20 mL) at room temperature overnight under argon atmosphere. The reaction mixture was then taken up in EtOAc, and washed sequentially with NH$_4$Cl(sat'd), water, and brine. The organic layer was dried with MgSO$_4$, filtered and the solvent evaporated in vacuo to yield 4-(1,3-dimethyl-6,7-dihydrobenzo[c]thiophen-4-yl)-1-trityl-1H-imidazole (1.6 g, overall 62%). 4-(1,3-Dimethyl-6,7-dihydrobenzo[c]thiophen-4-yl)-1-tritylimidazole (0.40 g, 0.8 mmol) and formic acid (5 mL, 0.13 mol) were stirred at room temperature for 18 hours. The reaction was partitioned between methylene chloride and $Na_2CO_3$ (sat'd). The organic layers were combined and dried with $MgSO_4$, filtered and the solvent was evaporated in vacuo. The resultant product was purified by chromatography on silica gel eluted with 10% MeOH/EtOAc (2–3 drops $NH_4OH$) to yield 4-(1,3-dimethyl-6,7-dihydrobenzo[c]thiophene-4-yl)-1H-imidazole (0.15 g, 82%). $^1H$ NMR ($CD_3OD$) δ1.75 (s, 3H), 2.26 (s, 3H), 2.31 (t, 2H), 2.55 (t, 2H), 6.01 (t, 1H), 6.92 (s, 1H), 7.61 (s, 1H). This material (0.25 g 1.08 mmol) was dissolved in hot isopropanol (25 mL) and added to maleic acid (0.125 g, 1.08 mmol) with stirring for 10 min. After cooling the crystals of Cp-4 were collected by filtration (0.23 g, 62%), mp 179–180° C. $^1H$ NMR (DMSO) δ1.75 (s, 3H), 2.28 (s, 3H), 2.40 (t, 2H), 2.55 (t, 2H), 6.05 (s, 2H) 6.18 (t, 1H), 7.55 (s, 1H), 8.75 (s, 1H). MS m/e 231 (M+H).

EXAMPLE 1A 4-(1,3-dimethyl-6,7-dihydrobenzo[c]thiophen-4-yl)-1-tritylimidazole

Intermediate of Example 1

Alternatively, a key intermediate for the preparation of Cp-4 was obtained by the following method. A solution of 1,3-dimethyl-4-keto-4,5,6,7-tetrahydrothionaphthene (3.78 g, 21 mmol) in dichloroethane was treated with 2,6-di-t-butyl-4-methyl pyridine (5.3 g, 26 mmol) at 0° C. under nitrogen atmosphere. After 15 min trifluoromethanesulfonic anhydride (4.11 mL, 24 mmol) was added dropwise to the reaction and stirred overnight at room temperature under nitrogen. The solvent was evaporated in vacuo and the residue was triturated with pentane. This eluant was filtered through silica gel to afford 1,3-dimethyl-6,7-dihydrobenzo[c]thiophen-4-yl trifluoromethanesulfonate as a clear oil (3 g, 46%). $^1H$ NMR ($CDCl_3$) δ2.28 (s, 3H), 2.42 (t, 2H), 2.50 (s, 3H), 2.58 (t, 2H), 5.81 (t, 1H). A solution of this material (1.6 g, 5.12 mmol) and dioxane (150 mL) was added to 4-(tributyltin)-1-trityl-1H-imidazole (3.7 g, 5.12 mmol, prepared as described by Stille, *Org. Synth.*, 1989, 68, 116), LiCl (0.65 g, 15.4 mmol), $(Ph_3P)_4Pd$ (0.107 g, 0.09 mmol), and 2,6-di-t-butyl-4-methylphenol (0.002 g, 0.009 mmol). The reaction was deoxygenated with Argon and refluxed overnight. A solution of 30% KF/ether (1:1) was added and stirred overnight at room temperature. The reaction mixture was filtered through a plug of silica, rinsed with ethyl acetate (300 mL), extracted sequentially with $NaHCO_3$ (sat'd), $H_2O$, brine, dried with $MgSO_4$, filtered and the solvent evaporated in vacuo to yield an oily residue. Crystals were precipitated with methylene chloride/hexane (80:20) and collected by filtration to yield 4-(1,3-dimethyl-6,7-dihydrobenzo[c]thiophen-4-yl)-1-trityl-1H-imidazole (1.7 g, 70%). Alternatively, 4-(1,3-dimethyl-6,7-dihydrobenzo[c]thiophen-4-yl)-1-tritylimidazole can be prepared by treating a solution of 4-iodo-1-tritylimidazole (1.4 g, 3.2 mmol, prepared as described by Turner and Lindel, *J. Org. Chem.* 1991, 56, 5739–5740) and methylene chloride (500 mL) at 0° C. with ethyl magnesium bromide (1.5 mL, 4.5 mmol). The reaction was stirred 15 min and then warmed to room temperature for 15 min. Ultrapure $ZnCl_2$ (871 mg, 6.4 mmol) was added to the reaction mixture and stirred for 40 min. A solution of 1,3-dimethyl-6,7-dihydrobenzo[c]thiophen-4-yl trifluoromethanesulfonate (1.4 g, 3.2 mmol) in THF (30 mL) was added to the reaction, followed by $Pd(PPh_3)_4$ (0.185 g, 0.16 mmol). The reaction was purged with Argon for 10 min and heated to reflux for 15 hrs. The reaction was washed with 1N HCl followed by $Na_2CO_3$ (sat'd). The organic layer was dried with $Na_2SO_4$, filtered and the solvent evaporated in vacuo to yield 4-(1,3-dimethyl-6,7-dihydrobenzo[c]thiophen-4-yl)-1-tritylimidazole (1.2 g, 80%). mp 205–207° C. $^1H$ NMR ($CDCl_3$) δ1.78 (s, 3H), 2.25 (s, 3H), 2.26 (t, 2H), 2.55 (t, 2H), 6.20 (t, 1H), 6.73 (s, 1H), 7.28 (m, 6H), 7.35 (m, 9H), 7.45 (s, 1H). Anal. calcd for $C_{32}H_{28}N_2S \cdot 0.5H_2O$: C, 79.80; H, 6.07; N, 5.82. Found: C, 79.42; H, 5.85; N, 5.62. MS m/e 473 (M+H), 243 (Tr), 165.

EXAMPLE 2

4-(Thionaphth-4-yl)-1H-imidazole (Z)-2-butenedioate (Cp-1)

2-(2-Bromoethyl)-1,3-dioxolane (2.9 mL, 25 mmol) was added to Mg (0.7 g, 29 mmol) and THF (50 mL) and heated to 30° C. for 1.5 h under nitrogen atmosphere. A solution of thiophen-3-yl-(1-tritylimidazol-4-yl)methanone (4.69 g, 11.2 mmol) in THF (15 mL) was added slowly and the reaction was heated for 18 h at 30° C. The reaction was diluted with EtOAc, washed with $NH_4Cl$ (sat'd), water, and brine. The organic layer was dried with $MgSO_4$, filtered and the solvent was evaporated in vacuo to yield 3-(1,3-dioxan-2-yl)-1-(1-tritylimidazol-4-yl)-1-(thiophen-3-yl)-propan-1-ol as ton crystals (6.01 g, 90%). mp 120–123° C. A solution of this material (1 g, 1.86 mmol) in dichloroethane (10 mL) was added to trimethylsilyl trifluoromethanesulfonate (0.36 mL, 18.6 mmol) and dichloroethane (50 mL) at 0° C. After stirring for 3 h at 25° C. the reaction mixture was cooled to 0° C. and treated with $Na_2CO_3$ (sat'd). The organic layer was dried with $MgSO_4$, filtered and solvent was evaporated in vacuo. Purification by chromatography using EtOAc/MeOH/$NH_4OH$, 98:1.9:0.1 as eluant afforded 4-(thionaphth-4-yl)imidazole (0.146 g, 40%). $^1H$ NMR ($CD_3OD$) δ7.31 (t, 1H), 7.40 (s, 1H), 7.60 (d, 1H), 7.61 (d, 1H), 7.77 (d, 1H), 7.80 (s, 1H), 7.83 (d, 1H). This material (0.146 g, 0.73 mmol) was dissolved in hot isopropyl alcohol (4 mL) and treated with maleic acid (0.847 g, 0.73 mmol) to yield Cp-1 (0.23 g, 100%) mp 173–174° C. $^1H$ NMR (DMSO) δ6.12 (s, 2H), 7.45 (t, 1H), 7.68 (d, 1H), 7.88 (d, 1H), 7.90 (d, 1H), 7.92 (s, 1H), 8.05 (d, 1H), 8.62 (s, 1H). MS m/e 201 (M+H), 100.

EXAMPLE 3

4-(4-Imidazoyl)-4,5,6,7-tetrahydrothianapthene Perchlorate (Cp-3)

At 0° C. methylmagnesium bromide (3M in ether, 7.56 ml, 22.7 mmol) was added by syringe to a stirred solution of 4-iodo-1-tritylimidazole (9.9 g, 22.7 mmol) in methylene chloride (200 mL) under an argon atmosphere. After 1 hr this solution was transferred by cannula to an addition funnel with a pressure equalizing sidearm, and then added dropwise to a magnetically stirred solution of 4-keto-4,5,6,7-tetrahydrothianapthene (3.45 g, 22.7 mmol) in methylene chloride (100 mL). After stirring overnight under a soft current of argon and at ambient temperature, the reaction was quenched with saturated, aqueous ammonium chloride (25 mL). The organic layer was separated, dried (magnesium sulfate), and concentrated. The resulting residue was triturated with ether and the solid collected by filtration to yield 4-hydroxy-4-[4-(1-tritylimidazoyl)]-4,5,6,7-tetrahydrothianapthene (6 g, 57%). $^1$H-NMR (CDCl$_3$) δ1.75–1.9 (m, 1H), 2.0–2.2 (m, 2H), 2.25 (t, 1H), 2.7–2.95 (m, 2H), 3.15 (s, 1H), 6.55 (s, 1H), 6.8 (d, 1H), 6.95 (d, 1H), 7.15 (m, 6H), 7.3 (m, 8H), 7.4 (s, 1H). Palladium hydroxide (2 g), hydrochloric acid (1N, 1 eq., 8.6 mL), and 4-hydroxy-4-[4-(1-tritylimidazoyl)]-4,5,6,7-tetrahydrothianapthene (4 g, 8.6 mmol) in methanol (70 mL) were hydrogenated (50 psig H$_2$) at 55° C. for 72 hrs. The catalyst was filtered off, and the solvent removed. The residue was converted to a perchlorate salt which was recrystallized (ether/methanol) affording Cp-3 (1.17 g, 44%). $^1$H-NMR (DMSO-d$_6$) δ1.7–1.9 (m, 3H), 2.15 (m, 1H), 2.8 (t, 2H), 4.2 (t, 1H), 6.65 (d, 1H), 7.3 (d, 1H), 7.35 (s, 1H), 905 (s, 1H). MS m/e 205 (M+1). Alternatively, Cp-3 (free base) could be prepared from Cp-2 by the following procedure. To a solution of the hydrochloride salt of Cp-2 (1.0 g, 0.004 mole) in 20 mL of methanol was added 250 mg of 10% Pd/C. The reaction mixture was hydrogenated at 45 psig for 6 hrs. The reaction mixture was filtered through Celite and the solvent was evaporated under reduced pressure to yield the product as a white powder. This powder was dissolved in 50 mL of water and the solution was made basic with Na$_2$CO$_3$. The aqueous solution was extracted with 2×20 mL of ethyl acetate. The combined organic layers were washed with brine and dried over K$_2$CO$_3$. The solvent was evaporated to yield the free base as a pale golden oil (0.72 g, 88%). $^1$H NMR (300 MHz, CD$_3$OD) δ1.8–2.1 (m. 4H), 2.8 (t, 2H), 4.05 (t, 1H, J=3.9 Hz), 6.6 (s, 1H), 6.6 (d, 1H, J=5.2 Hz), 7.05 (d, 1H, J=5.2 Hz), 7.6 (s, 1H).

EXAMPLE 4

4-(4-Imidazoyl)-6,7-dihydrothianapthene Perchlorate (Cp-2)

Concentrated hydrochloric acid (1 mL), and 4-hydroxy-4-[4-(1-tritylimidazoyl)]-4,5,6,7-tetrahydrothianapthene (2 g, 4.3 mmol) in methanol (20 mL) were refluxed for 16 hrs. The solvent was removed and the residue partitioned between chloroform and aqueous hydrochloric acid (1N). The aqueous layer was separated, neutralized to a pH of 7 with aqueous sodium bicarbonate, and the extracted with chloroform. The organic layer was dried and concentrated. The remaining oil was converted into a perchlorate salt which was recrystallized (ether/methanol) to afford Cp-2 (0.99 g, 65%). $^1$H-NMR (DMSO-d$_6$) δ2.6 (m, 2H), 2.95 (t, 2H), 6.35 (t, 1H), 7.1 (d, 1H), 7.4 (d, 1H), 7.8 (s, 1H), 9.2 (s, 1H), 14.5 (s, broad, 1H). MS m/e 203 (M+1).

Alternatively, Cp-2 was prepared by the sequence of reactions described below. To a solution of 4-keto-4,5,6,7-tetrahydrothianaphthene (3.04 g, 0.02 mole) in 100 mL of methylene chloride was added 2,6-di-t-butyl-4-methylpyridine (4.93 g, 0.024 mole) and the clear reaction mixture was stirred at room temperature for 10 min. Trifluoromethanesulfonic anhydride (3.7 mL, 0.022 mole) was added dropwise via syringe and immediately the clear solution became brown with a slight amount of precipitate. Stirring was continued for 1.5 hrs. The solvent was evaporated under reduced pressure. Pentane was added to the residue and the precipitated solid was collected by filtration and washed with pentane. The filtrate and washings were evaporated under reduced pressure. The residue was purified by flash chromatography on silica gel eluting with 90:10 hexane/ethyl acetate. The vinyl triflate which formed was obtained as a clear, colorless oil, 4.54 g (90%). $^1$H NMR (300 MHz, CDCl$_3$) δ7.09 (d, J=5.2 Hz, 1H), 6.98 (d, J=5.2 Hz, 1H), 5.72 (t, J=4.7 Hz, 1H), 2.93 (t, J=8.9 Hz, 2H), 2.62 (m, 2H). Ethyl magnesium bromide (4.0 ml of 3.0 M solution in diethyl ether. 0.012 mole) was added to a solution of 1-trityl-4-iodoimidazole (2.52 g, 0.01 mole) in 100 mL of THF. The reaction mixture was stirred at room temperature for 45 min at which time TLC (70:30 hexane/ethylacetate) indicated the starting material was consumed. Zinc chloride (2.72 g, 0.02 mole) was added and the reaction mixture was stirred for 1 hr. During this time the clear yellowish solution became cloudy white. The vinyl triflate described above (2.52 g, 0.01 mole) was dissolved in 10 mL of THF and added via syringe. Tetrakis(triphenylphosphine)palladium (0) (0.580 g, 0.0005 mole) was then added and the reaction mixture was heated to reflux. After 2 hrs, TLC indicated that most of the starting triflate was gone. Heating was continued for 16 hrs. The reaction mixture was cooled and 50 mL of saturated NH$_4$Cl was added. The mixture was extracted with 2×100 mL of CH$_2$Cl$_2$. The combined organic layers were washed with brine (1×50 mL), dried over Na$_2$SO$_4$ and evaporated under reduced pressure. The residue was chromatographed on silica gel eluting with 70:30 hexane/ethyl acetate. The product was obtained as a tan solid, 4-[4-(1-tritylimidazoyl)]-6,7-dihydrothianapthene (3.37 g, 78%). $^1$H NMR (300 MHz, CDCl$_3$) δ7.5 (s, 1H), 7.2–7.4 (m, 15 H), 7.05 (d, J=5.2 Hz, 1H), 6.95 (d, 1H), 6.9 (s, 1H), 6.4 (t, 1H, J=4.5 Hz), 2.85 (t, 2H, J=8.6 Hz), 2.5 (m, 2H).

In another method for the preparation of Cp-2 , ethyl magnesium bromide (4.0 ml of 3.0 M solution in diethyl ether. 0.012 mole) was added to a solution of 1-trityl-4-iodoimidazole (2.52 g, 0.01 mole) in 50 ml of THF (or CH$_2$Cl$_2$). The reaction mixture was stirred at room temperature for 45 min at which time TLC (70:30 hexane/ethylacetate) indicated that starting material was consumed. Tributyltin chloride was added and the reaction mixture was stirred for an additional 2 hrs. The solvent was evaporated under reduced pressure and the residue was chromatographed on silica gel eluting with hexane. The 4-imidazole stannane which was obtained was a thick colorless oil which solidified under vacuum (5.2 g, 87%). $^1$H NMR (300 MHz, CDCl$_3$) δ0.8–1.05 (m, 9H), 1.3–1.4 (m, 12H), 1.5 (m, 6H), 6.75 (s, 1H), 7.1–7.2 (m, 6H), 7.4–7.5 (m, 9H), 7.6 (s, 1H). The vinyl triflate prepared above (2.52 g, 0.01 mole) was added via syringe to a solution of this imidazole stannane (5.97 g, 0.01 mole) in 100 mL of dioxane. Lithium chloride (1.27 g, 0.03 mole) was added and then tetrakis (triphenylphosphine) palladium (0) (0.580 g, 0.0005 mole)

was added. The reaction mixture was heated to reflux for 16 hrs. The reaction mixture was cooled, 50 mL of saturated KF was added and this mixture was stirred for 2 hrs. Methylene chloride (100 mL) was added, the organic layer was separated, washed with brine (1×50 mL), dried over $Na_2SO_4$ and evaporated under reduced pressure. The residue was chromatographed on silica gel eluting with 70:30 hexane/ethyl acetate. The product 4-[4-(1-tritylimidazoyl)]-6,7-dihydrothianapthene was obtained as a tan solid (2.89 g, 67%). This material (2.22 g, 0.005 mole) was suspended in 50 mL of methanol and 1.5 mL of concentrated HCl was added. The clear, pale yellow solution was heated at reflux for 4 hrs. The reaction mixture was cooled and the solvent was evaporated under reduced pressure. Methanol was added to the oily residue and evaporated two additional times. The residue was twice triturated with ether to remove the trityl byproduct. The yellowish solid was recrystallized from acetone to yield Cp-2 (free base) as a white solid (1.03 g, 86%). $^1$H NMR (300 MHz, $CD_3OD$) δ9.0 (s, 1H), 7.63 (s, 1H), 7.22 (d, 1H, J=5.2 Hz), 7.0 (d, 1H, J=5.2 Hz), 6.3 (t, 1H, J=4.5 Hz), 2.9 (t, 2H, J=8.6 Hz), 2.5–2.6 (m, 2H).

EXAMPLE 5

4-(1,3-Dimethyl-4,5,6,7-tetrahydrobenzo[c]thiophene-4-yl)-1H-imidazole (Z)-2-Butenedioate (Cp-5)

Cp-5 was prepared by hydrogenation of Cp-4 in a manner analogous to the preparation of Cp-3 from Cp-2.

EXAMPLE 6

(Cp-7)

Cp-7 was prepared in a manner analogous to the preparation of Cp-2 or Cp-4.

EXAMPLE 7

(Cp-6)

Cp-6 was prepared by hydrogenation of Cp-7 in a manner analogous to the preparation of Cp-3 from Cp-2.

What is claimed is:

1. A compound of the formula:

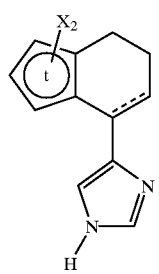

I wherein

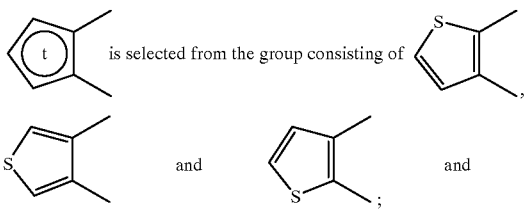

X is independently selected from the group consisting of hydrogen, $C_{1-4}$alkyl, bromine, chlorine, iodide, trifluoromethyl, $C_{1-4}$alkoxy, —$SO_2NH_2$ and nitro; with the stipulation that the six membered ring, except for the bond shared with thienyl, is fully saturated or has a single unsaturated bond in conjugation with the imidazole ring.

2. The compound of claim 1 which is an effective analgesic.

3. The compound of claim 1 which is an effective agent to treat hypertension, glaucoma, sexual dysfunction, depression, attention deficit hyperactivity disorder, the need for anesthesia and cardiac arrythmia.

4. The compound of claim 1 wherein X is selected from the group consisting of hydrogen, methyl, ethyl, n-propyl, bromine, chlorine, trifluoromethyl, methoxy, ethoxy, propoxy, —$SO_2NH_2$ and nitro.

5. The compound of claim 1 which is selected from the group consisting of:

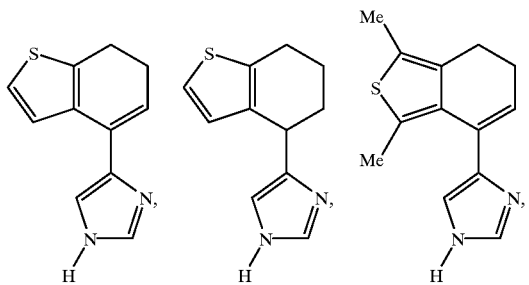

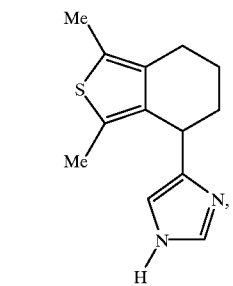

and

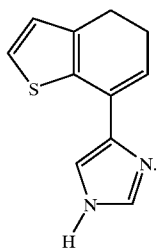

6. The compound of claim 1 which is a pharmaceutically acceptable salt of an inorganic or organic acid selected from the group consisting of hydrochloric, hydrobromic, hydroiodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benezenesulfonic, oxalic, pamoic, 2-naphthalenesulfonic, p-toluenesulfonic, cyclohexanesulfamic, salicylic and saccharic acid.

7. An analgesic formulation comprising an analgesically effective amount of a analgesically effective compound of claim 1 and a pharmaceutically effective carrier.

8. A formulation effective to treat hypertension, glaucoma, sexual dysfunction, depression, attention deficit hyperactivity disorder, the need for anesthesia and cardiac arrythmia comprising a compound of claim 1 effective to treat such condition in an effective amount and a pharmaceutically acceptable carrier.

* * * * *